(12) United States Patent
Govari et al.

(10) Patent No.: US 11,357,594 B2
(45) Date of Patent: Jun. 14, 2022

(54) JIG ASSEMBLED ON STEREOSCOPIC SURGICAL MICROSCOPE FOR APPLYING AUGMENTED REALITY TECHNIQUES TO SURGICAL PROCEDURES

(71) Applicant: JOHNSON & JOHNSON SURGICAL VISION, INC., Santa Ana, CA (US)

(72) Inventors: Assaf Govari, Haifa (IL); Vadim Gliner, Haifa (IL)

(73) Assignee: JOHNSON & JOHNSON SURGICAL VISION, INC., Irvine, CA (US)

(*) Notice: Subject to any disclaimer, the term of this patent is extended or adjusted under 35 U.S.C. 154(b) by 154 days.

(21) Appl. No.: 16/987,922

(22) Filed: Aug. 7, 2020

(65) Prior Publication Data

US 2022/0039904 A1    Feb. 10, 2022

(51) Int. Cl.
*A61B 90/00* (2016.01)
*H04N 13/254* (2018.01)
(Continued)

(52) U.S. Cl.
CPC .......... *A61B 90/37* (2016.02); *G02B 21/0012* (2013.01); *G02B 21/06* (2013.01); *G02B 21/22* (2013.01); *G06T 19/006* (2013.01); *H04N 13/239* (2018.05); *H04N 13/254* (2018.05); *H04N 13/341* (2018.05); *H04N 13/344* (2018.05); *A61B 2090/365* (2016.02);
(Continued)

(58) Field of Classification Search
None
See application file for complete search history.

(56) References Cited

U.S. PATENT DOCUMENTS 5,391,199 A    2/1995  Ben-Haim
6,239,724 B1   5/2001  Doron et al.
(Continued)

FOREIGN PATENT DOCUMENTS

KR    20160022110 A    2/2016
WO    WO9605768        2/1996

OTHER PUBLICATIONS

U.S. Appl. No. 16/856,696, filed Apr. 23, 2020.
U.S. Appl. No. 63/014,383, filed Apr. 23, 2020.
U.S. Appl. No. 63/014,402, filed Apr. 23, 2020.

*Primary Examiner* — Ryan M Gray
(74) *Attorney, Agent, or Firm* — Tamara Evans

(57) ABSTRACT

A system includes a first optical assembly (OA), a second OA and a processor. The first OA and second OA each coupled with a first and second microscope eyepiece, respectively. Each first and second OAs including a light source, configured to direct an emitted light beam (ELB) through the microscope toward an organ, and an image sensor, configured to sense a reflected light beam (RLB), which is reflected from the organ through the microscope, and to produce a signal indicative of the RLB. The processor is configured to control the first and second OAs to alternately direct the ELB and sense the RLB at first and second time intervals, and alternately display on a first display, during the first time intervals, images based on the signal from the first OA, and display on a second display, during the second time intervals, images based on the signal from the second OA.

11 Claims, 3 Drawing Sheets

(51) Int. Cl.
  *H04N 13/344* (2018.01)
  *H04N 13/341* (2018.01)
  *H04N 13/239* (2018.01)
  *G02B 21/00* (2006.01)
  *G02B 21/06* (2006.01)
  *G02B 21/22* (2006.01)
  *G06T 19/00* (2011.01)
  *A61F 9/007* (2006.01)

(52) U.S. Cl.
  CPC ... *A61B 2090/367* (2016.02); *A61B 2090/373* (2016.02); *A61B 2090/3762* (2016.02); *A61F 9/00745* (2013.01); *G06T 2210/41* (2013.01)

(56) References Cited

U.S. PATENT DOCUMENTS

| | | | |
|---|---|---|---|
| 6,332,089 | B1 | 12/2001 | Acker et al. |
| 6,484,118 | B1 | 11/2002 | Govari |
| 6,498,944 | B1 | 12/2002 | Ben-Haim et al. |
| 6,618,612 | B1 | 9/2003 | Acker et al. |
| 6,690,963 | B2 | 2/2004 | Ben-Haim et al. |
| 10,238,279 | B2 * | 3/2019 | Izatt ............ A61B 3/132 |
| 10,517,760 | B2 * | 12/2019 | Berlin ............ A61B 3/13 |
| 2002/0065455 | A1 | 5/2002 | Ben-Haim et al. |
| 2003/0120150 | A1 | 6/2003 | Govari |
| 2004/0068178 | A1 | 4/2004 | Govari |
| 2013/0208234 | A1 | 8/2013 | Lewis |
| 2014/0275760 | A1 | 9/2014 | Lee et al. |
| 2017/0164829 | A1 | 6/2017 | Awdeh |
| 2017/0227754 | A1 | 8/2017 | Huang |
| 2018/0008140 | A1 * | 1/2018 | Izatt ............ H04N 13/344 |
| 2018/0055356 | A1 | 3/2018 | Shibata et al. |
| 2018/0220100 | A1 * | 8/2018 | Ovchinnikov ..... H04N 5/44504 |
| 2018/0228392 | A1 | 8/2018 | Govari et al. |
| 2019/0015167 | A1 * | 1/2019 | Draelos ............ A61B 34/76 |
| 2019/0325785 | A1 | 10/2019 | Huang et al. |
| 2021/0315662 | A1 * | 10/2021 | Freeman ............ G06F 3/013 |
| 2021/0325649 | A1 * | 10/2021 | Segev ............ A61B 3/0008 |
| 2021/0330393 | A1 * | 10/2021 | Govari ............ G06T 7/0012 |
| 2021/0335483 | A1 * | 10/2021 | Freeman ............ G16H 40/67 |
| 2021/0382559 | A1 * | 12/2021 | Segev ............ H04N 5/23216 |
| 2022/0057645 | A1 * | 2/2022 | Huang ............ H04N 13/254 |

* cited by examiner

JIG ASSEMBLED ON STEREOSCOPIC SURGICAL MICROSCOPE FOR APPLYING AUGMENTED REALITY TECHNIQUES TO SURGICAL PROCEDURES

FIELD OF THE INVENTION

The present invention relates generally to medical devices, and particularly to methods and systems for stereoscopic imaging and augmented reality techniques used in ophthalmic procedures.

BACKGROUND OF THE INVENTION

During a minimally invasive medical procedure, such as an ophthalmic procedure, a surgeon navigates a medical instrument to a target location within a patient eye. In some cases, an augmented reality image, which is overlaid on a region of interest, may assist the surgeon to carry out the ophthalmic procedure. Various techniques have been developed for visualizing medical procedures using augmented reality techniques.

For example, U.S. Patent Publication No. 2018/0220100 describes a system including an augmented reality device communicatively coupled to an imaging system of an ophthalmic microscope. The augmented reality device may include a lens configured to project a digital image, a gaze control configured to detect a focus of an eye of an operator, and a dimming system communicatively coupled to the gaze control and the outer surface. The system including a processor that receives a digital image from the imaging system, projects the digital image on the lens, receives a signal from the gaze control regarding the focus of the eye of the operator, and transitions the outer surface of the augmented reality device between at least partially transparent to opaque based on the received signal.

U.S. Patent Publication No. 2019/0325785 describes an augmented reality training system, which includes a manipulation platform, an augmented reality stereo microscopic assembly, an instrument tracking module and a simulation generation module. The augmented reality stereo microscopic assembly is configured for camera-based capture of real stereo videos and for optical transmission of augmented reality images into the user's eyes.

U.S. Patent Publication No. 2014/0275760 describes an augmented reality image display system that may be implemented together with a surgical robot system. The augmented reality image display system including a camera capturing a real image having a plurality of markers attached to the patient's body or a human body model. The augmented reality image system may include an augmented reality image generator which detects the plurality of markers in the real image, estimates the position and gaze direction of the camera using the detected markers, and generates an augmented reality image by overlaying a region of the virtual image over the real image, and a display which displays the augmented reality image.

SUMMARY OF THE INVENTION

An embodiment of the present invention that is described herein provides a system including a first optical assembly (OA), a second OA and a processor. The first OA is coupled with a first eyepiece of a stereoscopic microscope (SM), the first OA including: (i) a first light source, configured to direct a first emitted light beam (ELB) through the SM toward an organ of a patient, and (ii) a first image sensor, configured to sense a first reflected light beam (RLB), which is reflected from the organ through the SM, and to produce a first signal indicative of the first RLB. The second OA is coupled with a second eyepiece of the SM, the second OA including: (i) a second light source, configured to direct a second ELB through the SM toward the organ, and (ii) a second image sensor, configured to sense a second RLB, which is reflected from the organ through the SM, and to produce a second signal indicative of the second RLB. The processor is configured to (a) control the first and second OAs to alternately: (i) direct the first ELB and sense the first RLB at first time intervals, and (ii) direct the second ELB and sense the second RLB at second different time intervals, and (b) alternately: (i) display on a first display, during the first time intervals, first images based on the first signal, and (ii) display on a second display, during the second time intervals, second images based on the second signal.

In some embodiments, the system including an augmented reality head mount display (ARHMD), which includes the first and second displays, and configured to display, to a user of the ARHMD having a gaze on a scene, images that are made of the first image and the second image overlaid of the scene. In other embodiments, the first light source includes a first infrared (IR) light source configured to emit a first IR ELB (IRELB), and a first visible light source configured to emit a first visible ELB (VELB), the second light source includes a second IR light source configured to emit a second IRELB, and a second visible light source configured to emit a second VELB, and the processor is configured to control: (i) the first OA to alternately direct, within the first time intervals, the first IRELB at third time intervals and the first VELB at fourth time intervals, and (ii) the second OA to alternately direct, within the second time intervals, the second IRELB at fifth time intervals and the second VELB at sixth time intervals. In yet other embodiments, the first signal includes a first IR signal and a first visible signal, and the second signal includes a second IR signal and a second visible signal, and the processor is configured to display: (i) in the first images, a first IR image, which is produce based on the first IR signal and is overlaid on a first visible image produced based on the first visible signal, and (ii) in the second images, a second IR image, which is produce based on the second IR signal and is overlaid on a second visible image produced based on the second visible signal.

In an embodiment, at least one of the first image sensor and the second image sensor includes a charge-coupled device (CCD). In another embodiment, the organ includes an eye of the patient.

There is additionally provided, in accordance with an embodiment of the present invention, a method including controlling a first optical assembly (OA) and a second OA to alternately: (i) direct a first emitted light beam (ELB) through a stereoscopic microscope (SM) toward an organ of a patient, and sense a first reflected light beam (RLB), which is reflected from the organ through the SM at first time intervals, and (ii) direct a second ELB through the SM toward the organ and sense a second RLB, which is reflected from the organ through the SM at second different time intervals. A first display and a second display are controlled to alternately (i) display on the first display, during the first time intervals, first images based on the first signal, and (ii) display on the second display, during the second time intervals, second images based on the second signal.

The present invention will be more fully understood from the following detailed description of the embodiments thereof, taken together with the drawings in which:

DETAILED DESCRIPTION OF EMBODIMENTS

Overview

Figure 1:
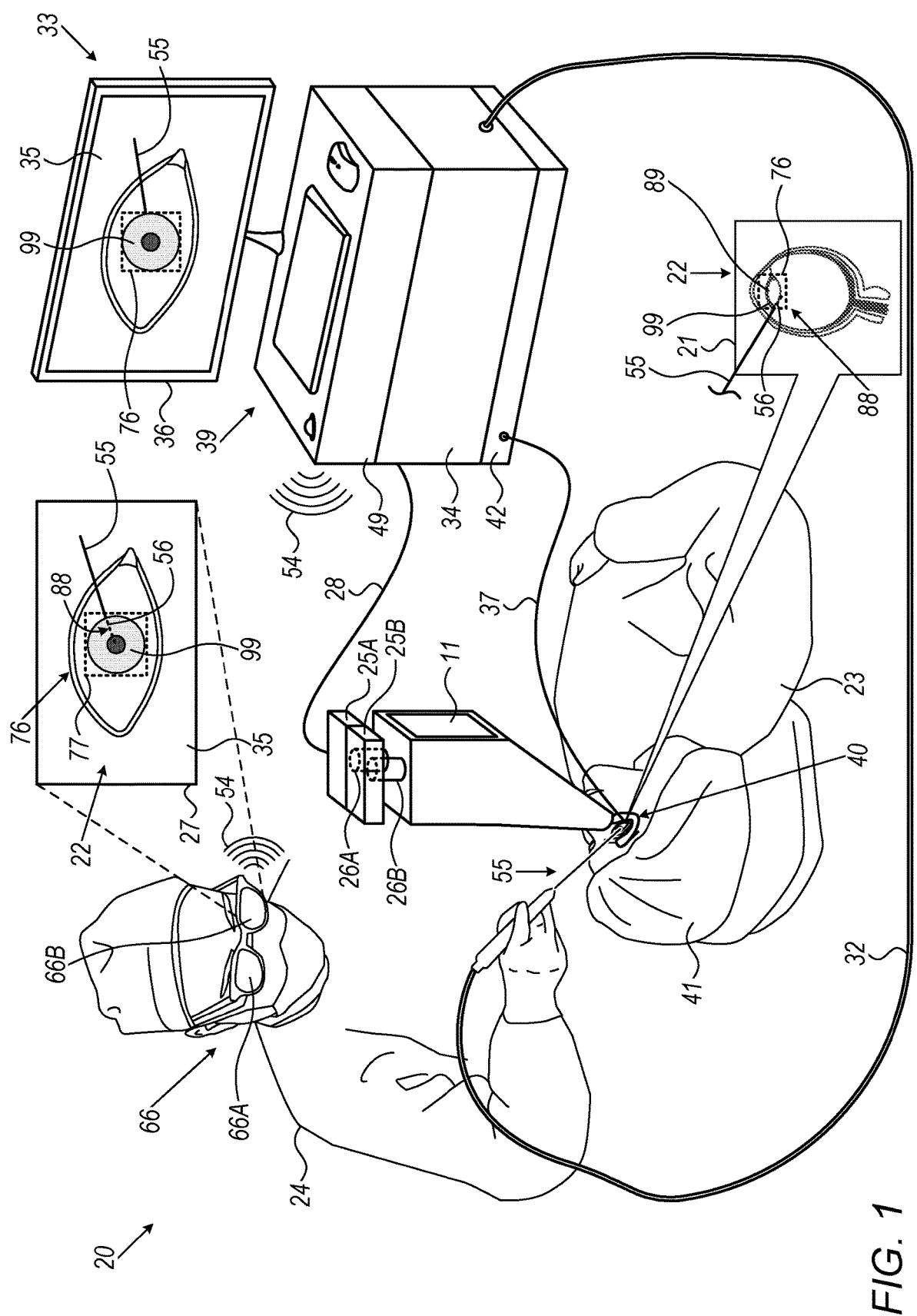
FIG. 1 is a schematic pictorial illustration of an ophthalmic surgical system, in accordance with an embodiment of the present invention.

Embodiments of the present invention that are described hereinbelow provide improved techniques for providing a surgeon with a three-dimensional effect by adding a depth imaging during an ophthalmic surgical procedure.

In some embodiments, an ophthalmic surgical system comprises a jig assembled on a stereoscopic ophthalmic surgical microscope, also referred to herein as a surgical microscope or stereoscopic microscope (SM) for brevity.

In some embodiments, the jig comprises two similar optical assemblies (OAs), referred to herein as first and second OAs, which are mounted respectively, on first and second eyepieces, typically used for the left and right eyes of a user of the SM. Each OA comprises a light source, configured to direct one or more emitted light beam(s) (ELBs) through the SM toward an eye of a patient, and an image sensor, such as a charge-coupled device (CCD), configured to sense a reflected light beam (RLB), which is reflected from the patient eye through the SM. The CCD is configured to produce a signal indicative of the RLB. For the sake of conceptual clarity, the description includes some indexing, such that the first OA directs a first ELB, senses a first RLB, and produces a first signal, and the second OA directs a second ELB, senses a second RLB, and produces a second signal.

In some embodiments, the ophthalmic surgical system comprises a processor, which is configured to control the first and second OAs, to alternately: (i) direct the first ELB and sense the first RLB at first time intervals, and (ii) direct the second ELB and sense the second RLB at second time intervals, different from the first time intervals. Note that one of the OAs is typically at an idle state (e.g., turned off) while the processor controls the other OA. The time intervals are typically on the order of milliseconds, but any other suitable time intervals may be used.

In some embodiments, the ophthalmic surgical system comprises a head mount display (HMD) having separate displays for the right and left eyes of the surgeon, referred to herein as first and second displays. The displays of the HMD are at least partially transparent, so that the HMD is configured to use augmented reality techniques for improving the visualization of a patient eye and/or surgical ophthalmic instruments used during the ophthalmic procedure.

In some embodiments, the processor is configured to alternately: (i) display on the first display, during the first time intervals, first two-dimensional (2D) images based on the first signal, and (ii) display on the second display, during the second time intervals, second 2D images based on the second signal. Note that alternating the display between the surgeon's right and left eyes, provides the surgeon with a three-dimensional (3D) effect that adds an illusion of visual depth that cannot be achieved by each of individual 2D first and second images received from the first and second OAs, respectively.

In some embodiments, the light source is configured to direct toward the patient's eye two or more light beams having different wavelengths. For example, the first and second OAs may comprise, each, an infrared (IR) light source and a visible light source, controlled by the processor to direct IR ELB and visible ELB alternately within the first and second time intervals, respectively. In such embodiments, the processor receives from the CCD, during the respective alternating time intervals, an IR signal indicative of the IR light reflected from the patient eye responsively to the IR ELB, and a visible signal indicative of the visible light reflected from the patient eye responsively to the visible ELB.

In some embodiments, based on both the IR signal and visible signal, the processor may produce each of the first and second images as an IR image overlaid on a visible image displayed alternately on the first and second displays of the HMD.

The disclosed techniques improve the quality of ophthalmic and other surgical procedures by providing the surgeon with a controllable stereoscopic image overlaid on a scene using augmented reality techniques.

System Description

FIG. 1 is a schematic pictorial illustration of an ophthalmic surgical system 20, in accordance with an embodiment of the present invention. System 20 is configured to carry out various types of ophthalmic procedures, such as but not limited to a cataract surgery.

In some embodiments, system 20 comprises a medical instrument, such as but not limited to a phacoemulsification handpiece or any other suitable type of an ophthalmic surgical tool, referred to herein as a tool 55, used by a surgeon 24 to carry out the ophthalmic surgical procedure. Other surgical tools may comprise an irrigation and aspiration (I/A) handpiece, a diathermy handpiece, a vitrectomy handpiece, and similar instruments.

Reference is now made to an inset 21 showing a sectional view of the surgical procedure carried out in an eye 22 of a patient 23. In some embodiments, surgeon 24 applies tool 55 for treating eye 22, in the present example, surgeon 24 inserts a distal end 88 of tool 55 into a region-of-interest (ROI) 76 of eye 22. In the example of inset 21, during a cataract surgical procedure, surgeon 24 inserts tool 55 below iris tissue 99 so as to apply phacoemulsification to a lens 89 of eye 22.

In some embodiments, tool 55 comprises one or more position sensor(s) 56 of a magnetic position tracking system (PTS) described in detail below. At least one position sensor 56 may comprise a triple-axis sensor (TAS) made from three coils or a single-axis sensor (SAS) implemented on a printed circuit board (PCB) or using any other suitable technique. Magnetic position sensors are described in further detail, for example in U.S. Pat. Nos. 6,498,944 and 6,690,963, and in U.S. patent Publication No. 2018/0228392, whose disclosures are all incorporated herein by reference. The one or more position sensor(s) 56 may be located anywhere on tool 55, for example, anywhere on a shaft of the tool or a portion of the tool located near the treatment site. In the present example, position sensor 56 is coupled to distal end 88 of tool 55.

Additionally or alternatively, the PTS may comprise any other suitable type of PTS, such as but not limited to an optical-based PTS or an impedance-based PTS. In such embodiments, at least one position sensor 56 may have a suitable structure other than the one or more coils described above.

Reference is now made back to the general view of FIG. 1. In some embodiments, system 20 comprises a location pad 40, which may have a frame and a plurality of field-generators. Examples of location pad 40 are shown and described in detail in U.S. patent application Ser. No. 16/856,696, in U.S. Provisional Application 63/014,383 and in U.S. Provisional Application 63/014,402, whose disclosures are all incorporated herein by reference. In some embodiments, location pad 40 comprises a flexible substrate, which is configured to be attached to facial tissue (e.g., skin) of patient 23. In the context of the present disclosure, and in the claims, using the term "attached" means that, when head 41 of patient 23 is moved in a given offset, location pad 40 is moved in the same offset. In other words, location pad 40 and head 41 are considered to be a single rigid body.

In an embodiment, system 20 comprises the aforementioned magnetic position tracking system, which is configured to track the position of one or more position sensors, such as position sensor 56 located on tool 55 that is used for treating eye 22, and/or other position sensors coupled to tools inserted into head 41, eye 22, or into any other organ of patient 23. In an embodiment, the magnetic position tracking system comprises magnetic field-generators (not shown) fixed at respective positions of the aforementioned frame of location pad 40.

In some embodiments, position sensor 56 is configured to generate one or more position signals in response to sensing external magnetic fields generated by the field-generators of location pad 40. In some embodiments, a processor 34 (described in detail below) of system 20 is configured to estimate, based on the position signals, the position of tool 55, e.g. distal end 88, within ROI 76 of eye 22.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Publication Nos. 2002/0065455 A1, 2003/0120150 A1 and 2004/0068178 A1, whose disclosures are all incorporated herein by reference.

In some embodiments, system 20 comprises a console 33, which comprises a memory 49, and a driver circuit 42 configured to drive, via a cable 37, the field-generators with suitable signals so as to generate magnetic fields in a predefined working volume, such as in ROI 76 of eye 22.

In some embodiments, console 33 comprises processor 34, typically a general-purpose computer, with suitable front end and interface circuits for receiving the position signals from position sensor 56 coupled to tool 55. In the present example, processor 34 receives the position signals via a cable 32; and may use cable 32 for exchanging any suitable signals with other components of tool 55. Other means of transmitting and receiving signals known in the art are also contemplated, e.g. BLUETOOTH or other wireless connection. Console 33 further comprises input device 39 and a display 36 (which may also be, for example, a keyboard, touch screen graphical user interface, or the like).

In some embodiments, system 20 comprises an ophthalmic surgical microscope 11 also referred to herein as a stereoscopic microscope (SM), such as ZEISS OPMI LUMERA series or ZEISS ARTEVO series supplied by Carl Zeiss Meditec AG (Oberkochen, Germany), or any other suitable type of ophthalmic surgical microscope provided by other suppliers. Ophthalmic surgical microscope 11 is configured to produce stereoscopic images (typically optical as will be described in detail in FIG. 2 below) and two-dimensional (2D) optical images of eye 22. In some embodiments, system 20 comprises two optical assemblies (OAs) 25A and 25B coupled, respectively, to two eyepieces 26A and 26B of ophthalmic surgical microscope 11, and configured to acquire two respective optical images of eye 22 as will be shown and described in detail in FIG. 2 below.

In some embodiments, the coupling between OAs 25A and 25B and respective eyepieces 26A and 26B, may be carried out using a suitable jig shown and described in FIG. 2 below, or using any other suitable method and/or apparatus.

In some embodiments, processor 34 is configured to receive the optical images from OAs 25A and 25B, via a cable 28 (although other means of transmitting and receiving signals known in the art may be used), and, based on the received optical images, to display an optical image 35 on display 36. Note that processor 34 is configured to display in image 35: (i) a stereoscopic image by using two separate optical paths with two objectives and eyepieces 26A and 26B to provide slightly different viewing angles to two respective OAs 25A and 25B, or (ii) a 2D optical image, e.g., by using an optical image received from one selected OA 25A or OA 25B of system 20. Note that in most cases surgeon 24 may prefer using the stereoscopic image in such surgical applications.

As shown in the sectional view of inset 21, surgeon 24 inserts distal end 88 of tool 55 below iris tissue 99. Therefore, iris tissue 99 constitutes a blocking element for imaging distal end 88 in optical image 35. In other words, by looking at optical image 35 on display 36, surgeon 24 cannot see the location of distal end 88 due to the blocking element within ROI 76, so as to accurately emulsify lens 89 of eye 22.

In some embodiments, processor 34 is configured to receive, from an anatomical imaging system, such as a computerized tomography (CT) system (not shown), a three-dimensional (3D) anatomical image acquired prior to the ophthalmic procedure.

In some embodiments, system 20 comprises an optical head mount display (HMD) 66 using augmented reality techniques for visualizing distal end 88 of tool 55 overlaid on at least one of optical image 35 and the anatomical image, as described herein. In the context of the present disclosure and in the claims, the terms HMD and augmented reality HMD (ARHMD) are used interchangeably and refer to HMD 66. In some embodiments, HMD 66 comprises a first display 66A mounted in front of a first eye (e.g., right eye) of surgeon 24, and a second display 66B mounted in front of a second eye (e.g., left eye) of surgeon 24. Displays 66A and 66B are configured to display, respectively, to the right and left eyes of surgeon 24, images received from processor 34.

Reference is now made to an inset 27 showing a displayed augmented image described herein. In an embodiment, processor 34 is configured to select, from the 3D anatomical image, a 2D slice of the anatomical image comprising CT imaging of ROI 76, referred to herein as a CT image (CTI) 77.

As described above, distal end 88 of tool 55 may be invisible in optical image 35, for being obstructed by a blocking element (e.g., iris tissue 99, any other tissue structure, or a medical apparatus used in the ophthalmic procedure). In some embodiments, based on optical image 35, CTI 77, and the position signal received from position sensor 56, processor 34 is configured to display the position of distal end 88 unobstructed. In the example of inset 27, the visualization of distal end 88 is shown as a dashed line.

In some embodiments, HMD 66 and console 33 have wireless devices (not shown) configured to exchange wireless signals 54 for transferring, inter alia, the aforementioned augmented image and/or any suitable combination of image 35, CTI 77, and the position signals of position sensor 56.

In an embodiment, processor 34 is configured to display, on HMD 66, a visualization of distal end 88 overlaid on CTI 77. In the example of inset 27, processor 34 is configured to replace, in ROI 76, the section of the optical image with a corresponding CTI 77, or with any other suitable section of a slice of the CT image.

In some embodiments, using the augmented reality techniques, processor 34 is configured to display iris tissue (or any other blocking element) transparent, so as to display the position of distal end 88 unobstructed.

In some embodiments, processor 34 is configured to display, to surgeon 24 or to any other user of the ARHMD having a gaze on a scene (e.g., eye 22 of patient 23, or display 36), stereoscopic images that are made of one or more images overlaid of the scene, as will be described in detail in FIG. 2 below. Note that the stereoscopic image provides the user of HMD 66, in the present example surgeon 24, with a three-dimensional effect, adding an illusion of depth to flat images acquired separately by OA 25A and OA 25B.

In some embodiments, processor 34 is configured to register optical image 35 and the anatomical image (e.g., a slice comprising CTI 77) in a common coordinate system, such as a coordinate system of the position tracking system. In other words, processor 34 receives two or more of the following inputs: (a) the optical (2D or stereoscopic) image from ophthalmic surgical microscope 11, (b) the anatomical image from the CT system, and (c) the position signal (generated by position sensor 56) from the position tracking system. Subsequently, processor 34 processes at least some of the received inputs (for example, by producing optical image 35, and/or CTI 77, and registers the coordinate systems of optical image 35, CTI 77 and the position signals received from position sensor 56, in a common coordinate system (e.g., the coordinate system of the position tracking system).

In some embodiments, after performing the registration process described above, processor 34 is configured to track the position of distal end 88, based on position signals received from one or more position sensor(s) 56. Moreover, processor 34 is configured to visualize the position of distal end 88 overlaid on at least one of the registered CTI 77 and optical image 35. In the example of inset 27, processor 34 is configured to produce the aforementioned augmented image comprising: (a) CTI 77 displayed on the section of ROI 76, (b) optical image 35 displaying tool 55 and eye 22 surrounding the section of ROI 76, and (c) a visualization of distal end 88, overlaid on CTI 77 in the section of ROI 76. In the context of the present disclosure and in the claims, the terms "produce" and "generate" are used interchangeably, e.g., for signals and images made by one or more position sensor(s) 56, processor 34 and any other component of system 20.

In some embodiments, processor 34 is configured to transmit the augmented image shown in inset 27 and described above, to HMD 66 so that surgeon 24 can see eye 22 and a visualization of the estimated position of distal end 88 of tool 55.

In some embodiments, the augmented image shown in inset 27, provides surgeon 24 with a complete visualization of tool 55, including distal end 88. In other embodiments, in order to optimize the visualization of distal end 88 during the ophthalmic procedure, processor 34 is configured to dynamically control the size of ROI 76, automatically (e.g., based on the position and/or obstruction of distal end 88) or in response to an instruction received from surgeon 24 using input device 39.

In alternative embodiments, HMD 66 may comprise a processor (not shown), which is configured to carry out at least some of the operations carried out by processor 34 and described above. In such embodiments, at least some of the signals described above (e.g., optical images from ophthalmic surgical microscope 11, CTI 77 from processor 34 or the CTI from the CT system, the position signals from position sensor(s) 56) may be transmitted directly (wirelessly or via cables) to the processor of HMD 66, which may generate and display the augmented image on HMD 66. In yet other embodiments, the operations described above may be divided, using any suitable definition, between processor 34 and the processor of HMD 66, so that the augmented image is displayed on HMD 66 as described in detail above.

This particular configuration of system 20 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of ophthalmic and other minimally invasive and surgical systems.

Jig Assembled on Stereoscopic Surgical Microscope

Figure 2:
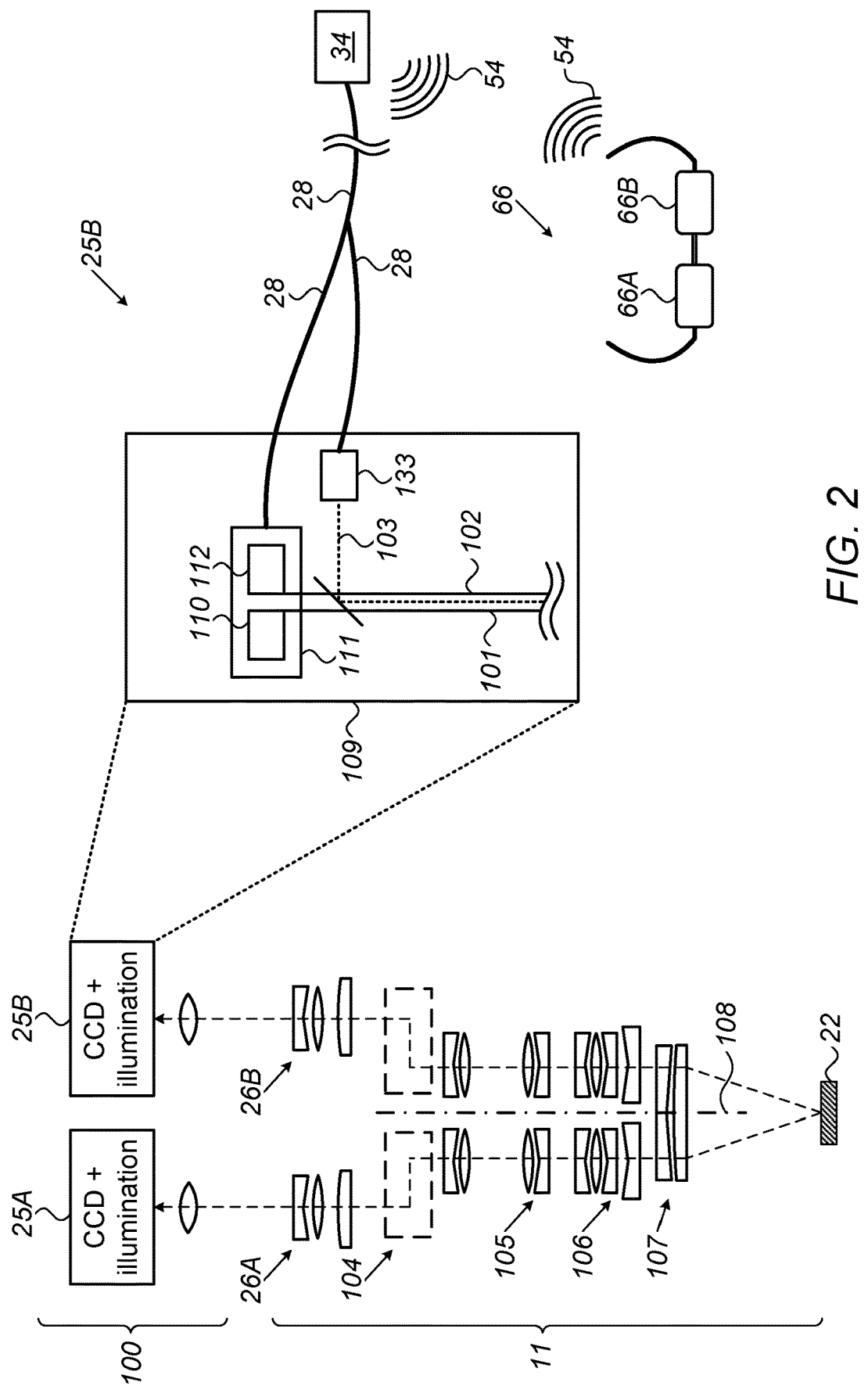
FIG. 2 is a schematic pictorial illustration of a jig assembled on a stereoscopic surgical microscope, in accordance with an embodiment of the present invention.

FIG. 2 is a schematic pictorial illustration of a jig 100 assembled on surgical microscope 11, in accordance with an embodiment of the present invention. In some embodiments, jig 100 comprises two similar optical assemblies 25A and 25B, coupled, respectively, with eyepieces 26A and 26B of surgical microscope 11.

In some embodiments, surgical microscope 11 may comprise any suitable type of ophthalmic surgical microscope as described in FIG. 1 above. In the present example, surgical microscope 11 comprises two separate optical paths, which are parallel to an optical axis 108 of surgical microscope 11, for conveying the ELBs and RLBs directed from and sensed by OAs 25A and 25B, respectively.

In some embodiments, for each optical path surgical microscope 11 comprises an eyepiece (e.g., eyepieces 26A and 26B), a prism assembly 104, a photo adaptor 105, a zooming assembly 106 for zooming in/out the first and second images (based on the signals) acquired by OAs 25A and 25B, respectively, wherein each zooming assembly comprising a set of multiple lenses moving relative to one another so as to enable the zoon in/out.

In some embodiments, surgical microscope 11 comprises a primary objective lens 107 that may comprise a set of one or more lenses, which is common to both optical paths and is configured to direct the ELBs from OAs 25A and 25B to ROI 76 of eye 22.

Reference is now made to an inset 109 showing optical assembly (OA) 25B. Note that the embodiments described herein of the structure and functionality of OA 25B are also applicable, mutatis mutandis, to OA 25A.

In some embodiments, OA 25B comprises a light source 111, which is configured to direct one or more emitted light beams (ELB) through surgical microscope 11 toward eye 22 of patient 23. In the present example, light source 111 comprises an infrared (IR) light source 110, configured to direct an IR ELB (IRELB) 101, and a visible light source 112, configured to direct a visible ELB (VELB) 102. In other embodiments, light source 111 may comprise any other suitable configuration of one or more light sources configured to direct any suitable wavelength or range of wavelengths.

In some embodiments, OA 25B comprises an image sensor, in the present example, a charge-coupled device (CCD) 133, which is configured to sense a reflected light beam (RLB) 103, which is reflected from eye 22 through surgical microscope 11. In some embodiments, in response to sensing RLB 103, CCD 133 is configured to produce a signal indicative of the sensed RLB 103.

In some embodiments, OA 25A (which is similar to OA 25B) also comprises light source 111 having IR light source 110 and visible light source 112, configured to direct IRELB 101 and VELB 102, respectively. In the context of the present disclosure and in the claims, light source 111 of OA 25A is also referred to herein as a first light source, whereas light source 111 of OA 25B is also referred to herein as a second light source. Similarly, the ELBs directed by light sources 111 of OA 25A and OA 25B, are also referred to herein as first and second ELBs, respectively, and the RLBs sensed by CCDs 133 of OA 25A and OA 25B, are also referred to herein as first and second RLBs, respectively.

In some embodiments, processor 34 is configured to control OAs 25A and 25B to alternately: (i) direct the first ELB and sense the first RLB (by OA 25A) at first time intervals, and (ii) direct the second ELB and sense the second RLB (by OA 25B) at second time intervals, which are different from the first time intervals. In other words, processor 34 is configured to switch between the activation of OAs 25A and 25B for producing first and second signals indicative of RLBs 103 sensed by CCDs 133 of OAs 25A and 25B, respectively.

In some embodiments, processor 34 is configured to alternately: (i) display on display 66A (also referred to herein as a first display) of HMD 66, during the aforementioned first time intervals, images (referred to herein as first images) of eye 22, which are produced based on the first one or more signals received from OA 25A, and (ii) display on display 66B (also referred to herein as a second display) of HMD 66, during the aforementioned second time intervals, other images (referred to herein as second images) of eye 22, which are produced based on the second one or more signals received from OA 25B.

In some embodiments, at each time interval, processor 34 is configured to synchronize between the directing of the ELB and the displaying of the image to the respective eye of surgeon 24. In other words, the toggling between the optical assemblies directing the light beam toward the patient eye, is synchronized with the toggling between the images displayed to surgeon 24 on each display of the augmented reality HMD.

In some embodiments, processor 34 is configured to control light source 111 of OA 25B to alternately direct, at different time intervals within the second time intervals, IRELB 101 and VELB 102 through surgical microscope 11 toward eye 22. In some embodiments, processor 34 is configured to receive from CCD 133 (i) an IR signal, indicative of an IR light beam reflected from eye 22 in response to directing IRELB 101 toward eye 22, and (ii) a visible signal, indicative of a visible light beam reflected from eye 22 in response to directing VELB 102 toward eye 22. In the context of the present disclosure and in the claims, CCD 133 of OA 25A is configured to produce "a first IR signal" and "a first visual signal," and CCD 133 of OA 25B is configured to produce "a second IR signal" and "a second visual signal."

In some embodiments, processor 34 is configured to produce an image based on the IR signal, referred to herein as an "IR-light image," and an image based on the visual signal, referred to herein as a "visible-light image." Processor 34 is configured to display the IR-light image and visible-light image, overlaid on display 66B. The same process is applied, within the first time intervals, to the components of OA 25A and to display 66A. Note that displays 66A and 66B of HMD 66 are at least partially transparent so that surgeon 24 can see the overlaid IR-light image and visible-light image on a scene of his/her gaze. For example, when surgeon 24 directs his/her gaze to patient eye 22 or to image 35 displayed on display 36.

In some embodiments, OA 25B is configured to exchange signals with processor 34. For example, (i) receiving from processor 34 control signals for directing IRELB 101 and/or VELB 102 from light source 111 toward eye 22, and (ii) transmitting to processor 34, the signal indicative of RLB 103. In the present example, the signal exchanging may be carried out over cable 28 shown in FIGS. 1 and 2, or using other suitable means of transmitting and receiving signals as described in FIG. 1 above.

In some embodiments, during the second time intervals processor 34 is configured to transmit, e.g., over wireless signals 54 or over a wire (not shown), the second images that may comprise at least one of the IR-light image and visible-light image, to display 66B of HMD 66. Note that the processes described above for OA 25B and processor 34 during the second time intervals, are applicable to OA 25A and processor 34 during the first time intervals, so that surgeon 24 can see the aforementioned augmented reality stereoscopic image displayed over HMD 66.

The configuration of jig 100 and surgical microscope 11 are simplified and provided by way of example, in order to illustrate certain problems that are addressed by embodiments of the present invention and to demonstrate the application of these embodiments in enhancing the performance of such an ophthalmic surgical system. Embodiments of the present invention, however, are by no means limited to this specific sort of example jig and/or surgical microscope and/or surgical system, and the principles described herein may similarly be applied to other sorts of ophthalmic and other minimally invasive surgical systems, and to image acquisition and processing systems thereof.

Figure 3:
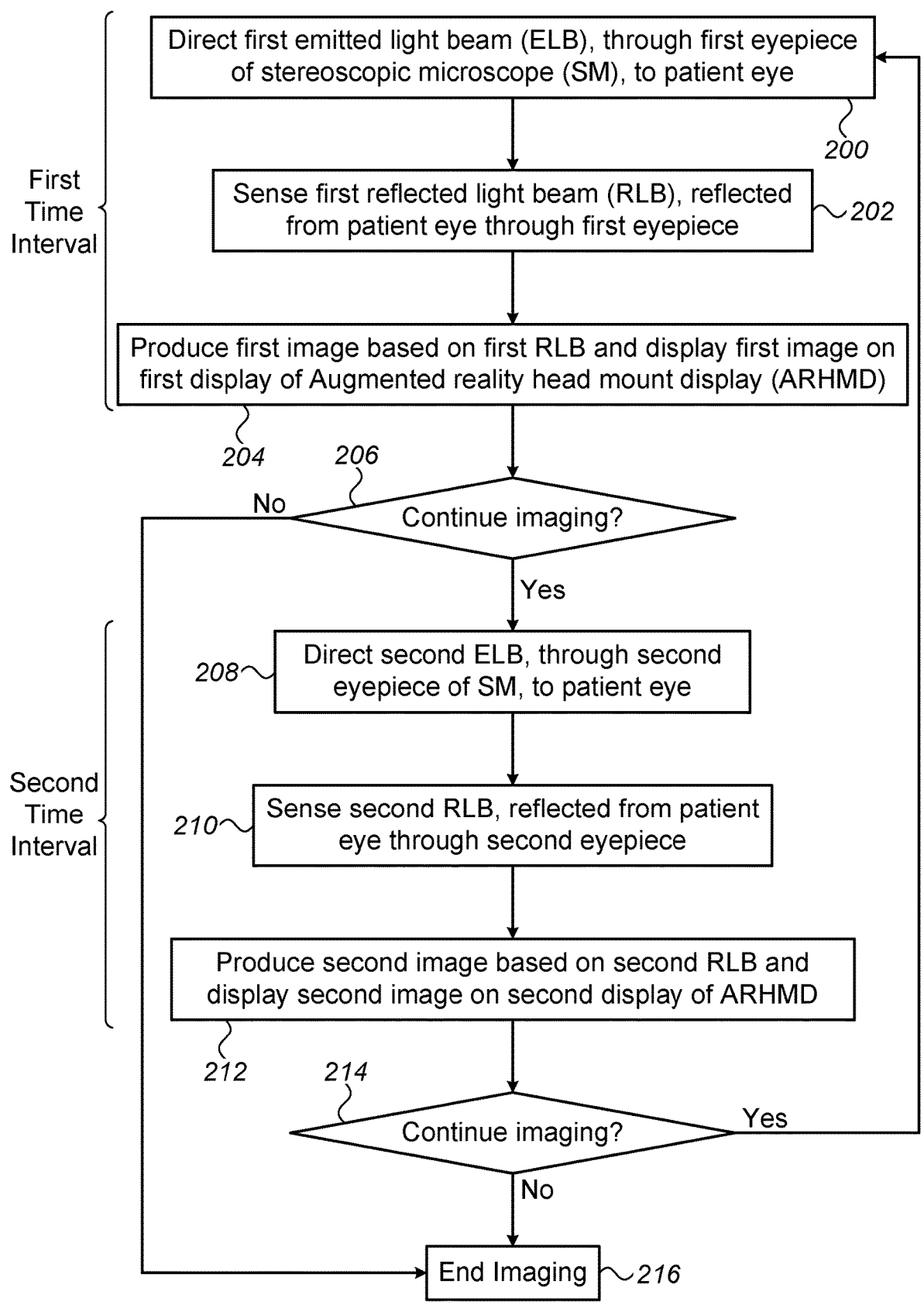
FIG. 3 is a flow chart that schematically illustrates a method for augmented-reality visualization of patient eye during an ophthalmic surgical procedure, in accordance with an embodiment of the present invention.

FIG. 3 is a flow chart that schematically illustrates a method for augmented-reality visualization of patient eye 22 during an ophthalmic surgical procedure, in accordance with an embodiment of the present invention. In the description below, the method is implemented on processor 34, but in other embodiments, the method may be implemented, mutatis mutandis, on any other suitable type of computing device or system.

The method begins at a first light beam directing step 200, with processor 34 controlling OA 25A to direct the first ELB (which may comprise at least one of IRELB 101 and VELB 102), through eyepiece 26A of surgical microscope 11, to patient eye 22. At a first light beam sensing step 202, processor 34 controls CCD 133 of OA 25A to: (i) sense the first RLB (e.g., RLB 103), reflected from patient eye 22 through eyepiece 26A, and (ii) produce the first signal (described in FIG. 2 above), which is indicative of RLB 103. In an embodiment, processor 34 is further configured to receive the first signal from OA 25A.

At a first image production step 204, processor 34 produces the first image (described in FIG. 2 above), which is based on the first RLB and first signal produced by OA 25A. Processor 34 is further configured to display the first image on display 66A of HMD 66. Note that steps 200, 202 and 204 are all carried out during the first time interval described in FIG. 2 above.

At a first decision step 206, processor 34 and/or surgeon 24 may check whether additional imaging is required to carry out the ophthalmic procedure. In case no more imaging is required, the method continues to an imaging ending step 216, which terminates the method. Note that in order to obtain the aforementioned stereoscopic image, processor 34 must alternately display the first image on display 66A (during the aforementioned first time interval) and the second image on display 66B (during the second time interval described in FIG. 2 above). Thus, at decision step 206, processor 34 and/or surgeon 24 may decide to continue the imaging process and proceed to the second time interval.

At a second light beam directing step 208, processor 34 controls OA 25B to direct the second ELB (which may comprise at least one of IRELB 101 and VELB 102), through eyepiece 26B, to patient eye 22. At a second light beam sensing step 210, processor 34 controls CCD 133 of OA 25B to: (i) sense the second RLB (e.g., RLB 103), reflected from patient eye 22 through eyepiece 26B, and (ii) produce the second signal (described in FIG. 2 above), which is indicative of RLB 103. In an embodiment, processor 34 is further configured to receive the second signal from OA 25B.

At a second image production step 212, processor 34 produces the second image (described in FIG. 2 above), which is based on the second RLB and second signal produced by OA 25B. Processor 34 is further configured to display the second image on display 66B of HMD 66. Note that steps 208, 210 and 212 are all carried out during the second time interval described in FIG. 2 above. Moreover, during the first time interval, OA 25B is typically at an idle state and processor 34 is not displaying the second image on display 66B. Similarly, during the second time interval, OA 25A is typically at an idle state and processor 34 is not displaying the first image on display 66A.

At a second decision step 214, processor 34 and/or surgeon 24 may check whether additional imaging is required for the ophthalmic procedure.

In case additional imaging is required, the method loops back to step 200. Alternatively, in case no more imaging is required, the method continues to an imaging ending step 216, which terminates the method.

Although the embodiments described herein mainly address ophthalmic procedures, the methods and systems described herein can also be used in other applications, such as in any application that requires displaying stereoscopic images to a user, and particularly to various types of high-resolution surgical applications, such as spine surgery and brain surgery.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
a first optical assembly (OA), which is coupled with a first eyepiece of a stereoscopic microscope (SM), the first OA comprising: (i) a first light source, configured to direct a first emitted light beam (ELB) through the SM toward an organ of a patient, and (ii) a first image sensor, configured to sense a first reflected light beam (RLB), which is reflected from the organ through the SM, and to produce a first signal indicative of the first RLB;
a second OA, which is coupled with a second eyepiece of the SM, the second OA comprising: (i) a second light source, configured to direct a second ELB through the SM toward the organ, and (ii) a second image sensor, configured to sense a second RLB, which is reflected from the organ through the SM, and to produce a second signal indicative of the second RLB; and
a processor, which is configured to:
control the first and second OAs to alternately: (i) direct the first ELB and sense the first RLB at first time intervals, and (ii) direct the second ELB and sense the second RLB at second different time intervals; and
alternately: (i) display on a first display, during the first time intervals, first images based on the first signal, and (ii) display on a second display, during the second time intervals, second images based on the second signal.

2. The system according to claim 1, and comprising an augmented reality head mount display (ARHMD), which comprises the first and second displays, and configured to display, to a user of the ARHMD having a gaze on a scene, images that are made of the first image and the second image overlaid of the scene.

3. The system according to claim 1, wherein the first light source comprises a first infrared (IR) light source configured to emit a first IR ELB (IRELB), and a first visible light source configured to emit a first visible ELB (VELB), wherein the second light source comprises a second IR light source configured to emit a second IRELB, and a second visible light source configured to emit a second VELB, and wherein the processor is configured to control: (i) the first OA to alternately direct, within the first time intervals, the first IRELB at third time intervals and the first VELB at fourth time intervals, and (ii) the second OA to alternately direct, within the second time intervals, the second IRELB at fifth time intervals and the second VELB at sixth time intervals.

4. The system according to claim 3, wherein the first signal comprises a first IR signal and a first visible signal, and the second signal comprises a second IR signal and a second visible signal, and wherein the processor is configured to display: (i) in the first images, a first IR image, which is produce based on the first IR signal and is overlaid on a first visible image produced based on the first visible signal, and (ii) in the second images, a second IR image, which is produce based on the second IR signal and is overlaid on a second visible image produced based on the second visible signal.

5. The system according to claim 1, wherein at least one of the first image sensor and the second image sensor comprises a charge-coupled device (CCD).

6. The system according to claim 1, wherein the organ comprises an eye of the patient.

7. A method, comprising:
controlling a first optical assembly (OA) and a second OA to alternately: (i) direct a first emitted light beam (ELB) through a stereoscopic microscope (SM) toward an organ of a patient, and sense a first reflected light beam (RLB), which is reflected from the organ through the SM at first time intervals, and (ii) direct a second ELB through the SM toward the organ and sense a second RLB, which is reflected from the organ through the SM at second different time intervals; and
controlling a first display and a second display to alternately (i) display on the first display, during the first time intervals, first images based on the first signal, and (ii) display on the second display, during the second time intervals, second images based on the second signal.

8. The method according to claim 7, wherein displaying on the first and second displays comprises displaying, to a user of an augmented reality head mount display (ARHMD) having a gaze on a scene, images that are made of the first images and the second images overlaid of the scene.

9. The method according to claim 7, wherein directing the first ELB comprises directing a first infrared (IR) ELB (IRELB) and a first visible ELB (VELB), wherein directing the second ELB comprises directing a second IRELB and a second VELB, and comprising: (i) alternately directing, within the first time intervals, the first IRELB at third time intervals and the first VELB at fourth time intervals, and (ii) alternately directing, within the second time intervals, the second IRELB at fifth time intervals and the second VELB at sixth time intervals.

10. The method according to claim 9, wherein the first signal comprises a first IR signal and a first visible signal, and the second signal comprises a second IR signal and a second visible signal, and wherein controlling the first and second displays comprises displaying: (i) in the first images, a first IR image, which is produce based on the first IR signal and is overlaid on a first visible image produced based on the first visible signal, and (ii) in the second images, a second IR image, which is produce based on the second IR signal and is overlaid on a second visible image produced based on the second visible signal.

11. The method according to claim 7, wherein the organ comprises an eye of the patient.

\* \* \* \* \*